(12) United States Patent
Bercovici et al.

(10) Patent No.: US 10,281,427 B2
(45) Date of Patent: May 7, 2019

(54) METHODS OF ISOTACHOPHORESIS DETECTION

(71) Applicant: TECHNION RESEARCH & DEVELOPMENT FOUNDATION LTD., Haifa (IL)

(72) Inventors: Moran Bercovici, Haifa (IL); Merav Karsenty, Jerusalem (IL); Tally Rosenfeld, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 30 days.

(21) Appl. No.: 15/314,537

(22) PCT Filed: May 28, 2015

(86) PCT No.: PCT/IL2015/050559
§ 371 (c)(1),
(2) Date: Nov. 29, 2016

(87) PCT Pub. No.: WO2015/181829
PCT Pub. Date: Dec. 3, 2015

(65) Prior Publication Data
US 2017/0212077 A1    Jul. 27, 2017

Related U.S. Application Data

(60) Provisional application No. 62/004,382, filed on May 29, 2014.

(51) Int. Cl.
*G01N 27/447* (2006.01)
*B01L 3/00* (2006.01)
(Continued)

(52) U.S. Cl.
CPC .... *G01N 27/44791* (2013.01); *B01L 3/50273* (2013.01); *B01L 3/502715* (2013.01); *C12Q 1/6825* (2013.01); *G01N 27/4473* (2013.01); *G01N 27/44713* (2013.01); *G01N 27/44726* (2013.01); *G01N 27/44734* (2013.01); *G01N 27/44765* (2013.01); *G01N 27/44795* (2013.01);
(Continued)

(58) Field of Classification Search
CPC ....... G01N 27/44791; G01N 27/44765; G01N 27/4473; G01N 27/44734; G01N 27/44726; G01N 35/00871; G01N 2035/00346; G01N 2035/00237; C12Q 1/6825; B01L 3/502715; B01L 3/50273; B01L 2300/0627; B01L 2300/18; B01L 2400/0421
See application file for complete search history.

(56) References Cited

U.S. PATENT DOCUMENTS

| | | |
|---|---|---|
| 4,459,198 A | 7/1984 | Mizuno et al. |
| 2005/0121324 A1 | 6/2005 | Park et al. |
| 2012/0175258 A1 | 7/2012 | Mariella, Jr. |

OTHER PUBLICATIONS

Crystal M. Han et al: "Increasing hybridization rate and sensitivity of DNA microarrays using isotachophoresis", The Royal Society of Chemistry, vol. 14, No. 16, May 20, 2014, pp. 2958-2967.
(Continued)

*Primary Examiner* — J. Christopher Ball
(74) *Attorney, Agent, or Firm* — The Roy Gross Law Firm, LLC; Roy Gross (57) ABSTRACT

An isotachophoresis (ITP) apparatus, a kit comprising same and method of use thereof for the detection and/or separation of analytes of interest.

18 Claims, 5 Drawing Sheets

(51) Int. Cl.
*C12Q 1/6825* (2018.01)
*G01N 35/00* (2006.01)

(52) U.S. Cl.
CPC ............ *G01N 35/00871* (2013.01); *B01L 2300/0627* (2013.01); *B01L 2300/18* (2013.01); *B01L 2400/0421* (2013.01); *G01N 2035/00237* (2013.01); *G01N 2035/00346* (2013.01)

(56) References Cited

OTHER PUBLICATIONS

Merav Karsenty et al: "Current monitoring in microchannel with repeated constrictions for accurate detection of sample location in isotachophoresis", Analytical Chemistry, vol. 87, No. 1, Nov. 25, 2014, pp. 1-12.

METHODS OF ISOTACHOPHORESIS DETECTION

RELATED APPLICATIONS

This application is a national stage application under 371 of PCT/IL2015/050559 filed on May 28, 2015, and claims the benefit of U.S. Ser. No. 62/004,382 filed on May 29, 2014. The disclosure of both applications are incorporated herein by reference in their entirety.

FIELD OF INVENTION

The present invention is directed to; inter alia, automated isotachophoresis system for the detection and/or selection of analytes of interest.

BACKGROUND OF THE INVENTION

Surface-based biosensors are perhaps the most common type of sensors for biological targets such as nucleic acids and proteins. In most implementations, they are based on a "capturing probe" (e.g. an antibody or synthetic DNA sequence) which is immobilized on a surface, and to which targets specifically bind. Detection of the binding events can then be obtained in various ways, including for example fluorescence, electrochemical signals, or surface plasmon resonance (SPR).

Regardless of the binding or transduction mechanism, the sensitivity of all surface biosensors is fundamentally limited by the rate at which target molecules bind to the surface. Several factors, namely diffusion, transport, and reaction rates limit hybridization or binding at low concentrations. While diffusion and transport limitation can be effectively overcome by use of devices such as mixers and flow channels, reaction rates remain a major bottleneck toward achieving rapid binding of biomolecules at low concentrations. This is because hybridization and binding typically take the form of second order reactions, with reaction time inversely proportional to the concentration of the reactants (Squires, T. M., et al., 2008, Nat Biotechnol 26, 417-426). For example, surface-bound probes for nucleic acid capture are effectively employed in microarray technology. The main advantage of surface-bound probes are that they are easily multiplexed, thus enabling simultaneously screening for thousands or even up to 1 million biomarkers in a single experiment. However, the capture process is limited by both diffusion and slow reaction kinetics, and so incubation times typically exceed 24 hours. As a result, there is a growing need for methods that significantly accelerate reaction rates and lower detection time.

Figure 1A:
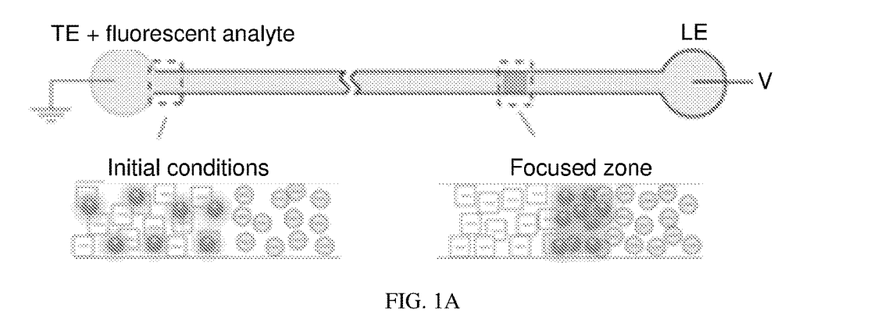
FIGS. 1a-c. Schematic of a typical ITP assay. (a) A simple microchannel is connected to two reservoirs and is initially filled with LE solution. (b) Analytes are mixed in the trailing electrolyte (TE) reservoir. (c) When an electric field is applied all ions electromigrate in the channel. The LE and TE are chosen such that analytes of interest have a higher mobility than the TE, but cannot overspeed the LE. This results in selective focusing at the sharp LE-TE interface.
Figure 1B:
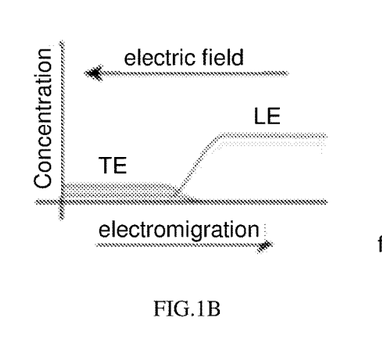
Figure 1C:
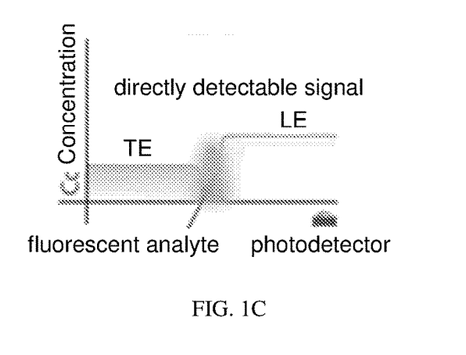

Isotachophoresis ("ITP") is an electrophoresis technique which allows for simultaneous separation and preconcentration of analytes based on their effective electrophoretic mobility. The process has been described repeatedly, as for instance, Bier and Allgyer, Electrokinetic Separation Methods 443-69 (Elsevier/North-Holland 1979). As illustrated in FIG. 1, ITP uses a discontinuous buffer system consisting of leading (LE) and terminating (TE) electrolytes. The LE and TE are chosen to have respectively higher and lower electrophoretic mobility than the analytes of interest. Sample is injected between the TE and LE (or can be mixed with the TE in the reservoir). When an electric field is applied, ions whose electrophoretic mobility is bracketed between that of the LE and TE focus within an electric field gradient at the LE-TE interface. Design of the LE and TE chemistries enables selective focusing of species of interest, and exclusion of undesired species. Up to a million-fold increase in concentration in 2 minutes has been demonstrated.

Figure 2A:
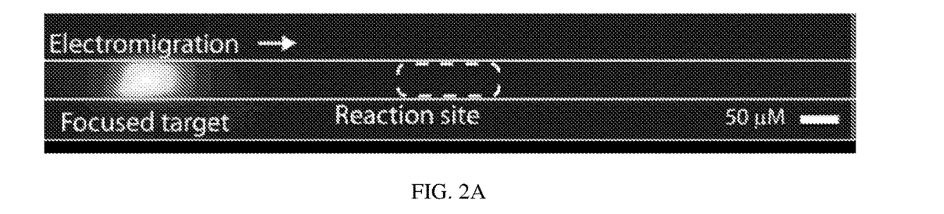
FIGS. 2a-c. Raw fluorescence images showing an experimental demonstration of ITP-based surface hybridization. (a) Fluorescent DNA oligonucleotides (used here for illustration purposes only) are focused 20,000-fold at the ITP interface and electromigrate toward the reaction zone pre-functionalized with complementary probes. (b) The ITP interface passes over the reaction zone allowing rapid hybridization of complementary strands. (c) The ITP interface leaves the reaction zone, carrying unhybridized free targets, leaving the surface in a clean buffer environment.
Figure 2B:
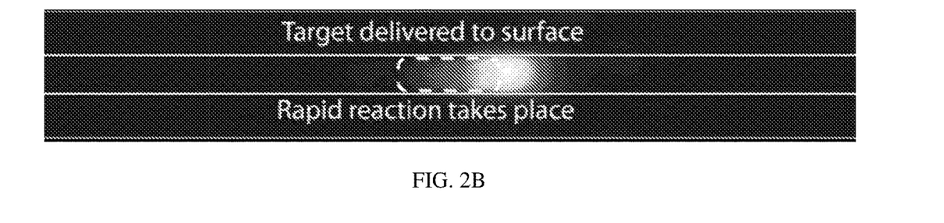
Figure 2C:
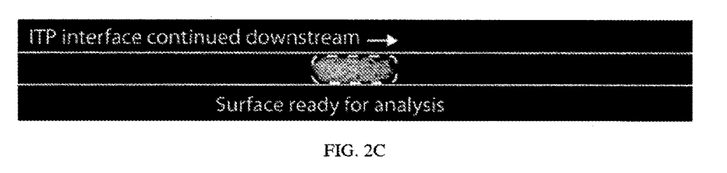

ITP is typically used to focus a sample of interest and deliver a high concentration target to a pre-functionalized surface, thus enabling rapid reaction at the sensor site. A recent publication showed two orders of magnitude improvement in limit of detection (LoD) compared to standard continuous flow-based hybridization, in a 3 min ITP-based nucleic acid hybridization assay (Karsenty et al., 2014, Analytical chemistry, 86(6), 3028-3036. As shown in FIG. 2, the ITP interface in which the sample is focused, transverses by electromigration over the reactive surface. However, despite a 20,000-fold increase in sample concentration, signal is enhanced only 100-fold due to the short reaction time (2 sec) in which the sample overlaps with the surface. Allowing longer reaction times is key in exhausting the full potential of the technique.

US 2012/0175258 provides an isotachophoresis system for separating a sample containing particles into discrete packets including a flow channel having a large diameter section and a small diameter section; a negative electrode operably connected to the flow channel; a positive electrode operably connected to the flow channel; a leading carrier fluid in the flow channel; a trailing carrier fluid in the flow channel; and a control for separating the particles in the sample into discrete packets using the leading carrier fluid, the trailing carrier fluid, the large diameter section, and the small diameter section.

Thus, there is an unmet need for fully automated ITP devices and methods of use thereof, such as for performing assays having significantly accelerate reaction rates and lower detection time of analytes of interest.

SUMMARY OF THE INVENTION

In one aspect, the present invention provides an ITP apparatus comprising:
(a) a flow channel comprising at least one first cross-section area and at least one second cross-section area, wherein the ratio between said at least one second cross-section area and said at least one first cross-section area is of 1:2-1:50;
(b) a first zone and a second zone, said first zone is configured to contain a solution of high effective mobility leading electrolyte (LE) ion, and said second zone is configured to contain a solution of low effective mobility trailing electrolyte (TE) ion;
(c) a control unit configured to modulate an ITP interface in response to a significant electric current or voltage change.

In another aspect, the present invention provides a system comprising:
(i) an ITP apparatus comprising:
(a) a flow channel comprising at least one first cross-section area and at least one second cross-section area, wherein the ratio between said at least one second cross-section area and said at least one first cross-section area is of 1:2-1:50, and
(b) a first zone and a second zone, said first zone is configured to contain a solution of high effective mobility leading electrolyte (LE) ion, and said second zone is configured to contain a solution of low effective mobility trailing electrolyte (TE) ion;
(ii) a measurement apparatus configured to measure electric current or voltage; and (iii) a control unit configured to modulate an ITP interface of said ITP apparatus in response to a significant electric current or voltage change.

In some embodiments, said ITP apparatus is a permanent ITP apparatus. In some embodiments, said ITP apparatus is a disposable ITP apparatus.

In another aspect, the present invention provides a method for detecting an analyte of interest, comprising the steps of:
(a) providing the ITP apparatus described herein;
(b) providing a sample including at least one analyte of interest to the flow channel of said ITP apparatus;
(c) applying an electric field across said first zone and said second zone;
(d) detecting a significant electric current or voltage change; and
(e) performing at least one function in response to the significant electric current or voltage change detected in step (d);
thereby detecting the analyte of interest of interest.

In some embodiments of the methods of the invention, said performing at least one function is performing at least one modulation of the ITP interface.

In some embodiments, the modulation of the ITP interface is selected from the group consisting of:
(i) substantially modulate the electric field for a pre-determined period of time;
(ii) apply a counter-flow for a pre-determined period of time;
(iii) modulate the temperature in a pre-determined zone in said flow channel;
(iv) add at least one compound or composition to a pre-determined zone in said flow channel; and
(v) a combination thereof.

In another embodiment, said substantially modulation of the electric field is substantially lowering the electric field. In another embodiment, said lowering the electric field is switching the electric field off. In another embodiment, said substantially modulation of the electric field is substantially elevating (increasing) the electric field. In another embodiment, said elevating the electric field is switching the electric field on. In another embodiment, said substantially modulation of the electric field is electric filed path switching.

In another embodiment, said significant electric current or voltage change is of at least 20% rate of change in said current or voltage. In another embodiment, said significant electric current change is a rapid current drop. In another embodiment, said significant electric current change is a rapid current increase.

In another embodiment, said ITP apparatus comprises at least one regulator selected from the group consisting of: (i) an electric field regulator; (ii) a counter-flow regulator; and (iii) a temperature regulator; or a combination thereof.

In another embodiment, the control unit is configured to perform at least one function subsequent to a significant current or voltage change. In another embodiment, the electric field control unit is configured to perform at least one function concurrent to a significant current or voltage change.

In another embodiment, the ITP apparatus of the invention comprises a plurality of first cross-section areas and second cross-section areas.

In another embodiment, said flow channel of the ITP apparatus of the invention is adapted to be operably connected to at least one anode and at least one cathode.

In another embodiment, the ITP apparatus of the invention comprises a second:first cross-section area ratio of 1:2-1:25. In another embodiment, said cross-section ratio is of 1:2-1:10. In another embodiment, said cross-section ratio is of 1:3-1:5. In another embodiment, said second cross-section width is in the range of 5-100 μm. In another embodiment, said second cross-section width is in the range of 10-50 μm. In another embodiment, said second cross-section has a length in the range of 20-500 μm.

In another embodiment, said at least one function or modulation of the ITP interface (e.g., substantially lowering the electric field for a pre-determined period) enables increased reaction time for detecting said analyte of interest. In another embodiment, the method of the invention further comprising step (f) comprising reestablishing the electric field of step (c).

In another embodiment, said analyte is selected from nucleic acid molecules or amino acid molecules, including peptides and proteins.

In another aspect there is provided a kit comprising (i) the ITP apparatus of the invention; (ii) a solution of high effective mobility leading electrolyte (LE) ion; and (iii) a solution of low effective mobility trailing electrolyte (TE) ion. In some embodiments, said kit is for detecting or selecting an analyte of interest. In another embodiment, the LE and TE solutions have respectively higher and lower electrophoretic mobility than the analyte of interest. In another embodiment, said kit further comprises instruction for use of said kit.

According to another aspect, there is provided a computer program product comprising a non-transitory computer-readable storage medium having program code embodied thereon, the program code executable by at least one hardware processor to:
(a) detect a significant electric current or voltage change in a flow channel comprising at least one first cross-section area and at least one second cross-section area, wherein the ratio between said at least one second cross-section area and said at least one first cross-section area is of 1:2-1:50; and
(b) perform at least one function in response to the significant electric current or voltage change detected in step (a).

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 4a-b. (a) Raw fluorescence images showing an experimental demonstration of our technique. We deliver the concentrated ITP zone to a desired chamber, using our automatic location detection technique (FIG. 2). Upon arrival, the electric field is turned off and the sample is allowed to react with the surface. After a fixed time allocated for reaction, the electric field is reestablished and the ITP interface continues electromigrating, removing any unreacted species from the surface. (b) Experimental results and model predictions comparing standard flow-through hybridization with ITP-based hybridization. Our model accurately predicted a 100-fold improvement in signal and limit of detection (LoD) in the case where the ITP zone purely electromigrates over the surface (without stopping). Using our "stop and diffuse" scheme our model predicts an additional 10-fold improvement, resulting in a 1000-fold improvement compared to a standard flow assay.

DETAILED DESCRIPTION OF THE INVENTION

The present invention provides, in some embodiments, an isotachophoresis (ITP) apparatus, a kit comprising same and method of use thereof for the detection and/or separation of analytes of interest.

The present invention is based, in part, on the finding that an ITP process may be automated by virtue of using a flow channel having unique geometrical properties (e.g., narrow constrictions) and measuring changes in the applied electric field. Without wishing to be bound by any theory or mechanism of action, a substantial change in the measured electric current or voltage indicates passage of the ITP interface through a transition region (e.g., transition between a wide and narrow section of the channel), which can respectively be used for performing one or more pre-defined functions on the ITP interface.

Typically, for a constant applied voltage, the current in ITP decreases monotonically due to increase in resistance. However, a rapid and significant current drop is observed upon entrance of the ITP interface into a constriction (FIG. 3b). In some embodiments, the significant current drop may be used for performing an action, including but not limited to, switching off the electric field. As a non limiting example, FIG. 4a demonstrates use of the ITP apparatus and method of the invention for delivering the concentrated ITP zone to a desired chamber, wherein upon arrival, the electric field is automatically turned off and the sample is allowed to diffuse, thereby enabling increased reaction rates. After a pre-defined time allocated for reaction, the electric field is reestablished and the ITP interface continues electromigrating, removing any un-reacted species from the surface. In some embodiments, a 10-fold improvement over previously known ITP-based assay, and a total of 1000-fold improvement compared to standard flow assay, is demonstrated.

A skilled artisan will appreciate that the ITP apparatus and method of the invention may apply constant voltage and detect current changes, or vice versa, apply constant current and detect voltage changes.

In some embodiments, the ITP apparatus and method of the invention are substantially automated, such as do not require a camera or any ITP-interface position detecting apparatus (e.g., optical apparatus).

In some embodiments, there is provided an isotachophoresis (ITP) kit comprising:
 (i) a disposable ITP apparatus comprising:
  (a) a flow channel comprising at least one first cross-section area and at least one second cross-section area, wherein the ratio between said at least one second cross-section area and said at least one first cross-section area is of 1:2-1:50, and
  (b) a first zone and a second zone, said first zone is configured to contain a solution of high effective mobility leading electrolyte (LE) ion, and said second zone is configured to contain a solution of low effective mobility trailing electrolyte (TE) ion;
 (ii) a measurement apparatus configured to measure electric current or voltage; and
 (iii) a control unit configured to modulate an ITP interface of said ITP apparatus in response to a significant electric current or voltage change.

In some embodiments, there is provided an isotachophoresis (ITP) system comprising:
 (i) a permanent ITP apparatus comprising:
  (a) a flow channel comprising at least one first cross-section area and at least one second cross-section area, wherein the ratio between said at least one second cross-section area and said at least one first cross-section area is of 1:2-1:50, and
  (b) a first zone and a second zone, said first zone is configured to contain a solution of high effective mobility leading electrolyte (LE) ion, and said second zone is configured to contain a solution of low effective mobility trailing electrolyte (TE) ion; and
 (ii) a measurement apparatus configured to measure electric current or voltage; and
 (iii) a control unit configured to modulate an ITP interface of said ITP apparatus in response to a significant electric current or voltage change.

In some embodiments, the apparatus of the invention, or the system of the invention, comprises an electric current or voltage sensor.

In some embodiments, the ITP system, apparatus, kit and method of the invention is useful for precise identification of ITP location. In some embodiments, said ITP system, apparatus, kit and method provide identification of ITP location with an accuracy of less than 100 microns, an accuracy of less than 90 microns, an accuracy of less than 80 microns, an accuracy of less than 70 microns, an accuracy of less than 60 microns, or an accuracy of less than 50 microns.

In another embodiment, identification of ITP location triggers or results in performing at least one pre-defined action. In another embodiment, said action performed in response to an electric current/voltage change is modulation of the ITP interface.

Non-limiting examples of pre-defined actions, which may be performed in response to an electric current/voltage change as described herein include:
(i) substantially modulating the electric field for a pre-determined period of time;
(ii) applying a counter-flow for a pre-determined period of time;
(iii) modulating the temperature in a pre-determined zone in said flow channel;
(iv) adding at least one compound or composition to a pre-determined zone in said flow channel;
(v) operating (e.g., turning on/off) a light source or imaging device; and
(vi) a combination of any one of (i)-(vi).

In another embodiment, the action performed in response to an electric current/voltage change is substantially modulating the electric field for a pre-determined period of time. In another embodiment, said modulating is reducing the electric field. In another embodiment, said modulating is switching the electric field off. In another embodiment, said modulating is enhancing the electric field.

In another embodiment, said modulating the electric field is modulating (or switching) the electric field path. In another embodiment, the said flow channel is a branched flow channel. In another embodiment, modulating the electric field path is applying an electric filed in the direction of a branch of the flow channel. In another embodiment, said branch is configured to contain a solution of leading electrolytes (LE). In another embodiment, said branch is configured to contain a solution of trailing electrolytes (TE). In another embodiment, modulating the electric field results in driving (flowing or electromigrating) the analyte to the branched channel. In another embodiment, the apparatus is configured to separate said analyte of interest. In another embodiment, the electric field is switched from a TE containing sample (i.e. a dirty reservoir) to a clean TE reservoir.

In another embodiment, the action performed in response to an electric current/voltage change is applying a counter-flow (e.g., a flow countering the electric field) for a pre-determined period of time. In another embodiment, said applied counter-flow is configured to maintain a non-migrating zone for the analyte (e.g., in the ITP interface). In another embodiment, the ITP apparatus and method of the invention further comprise flow generating means configured to generate flow countering the electromigration of the analyte of interest. In another embodiment, the flow generating means is adjusted to equally counter the flow of the analyte. In another embodiment, the flow generating means is responsible for maintaining a stationary portion (non-migrating zone for the analyte) of the ITP. In another embodiment the sum of ITP electromigration and counter-flow generated by the flow generating means with respect to analyte within the ITP system as described herein, is substantially zero.

In another embodiment, the flow generating means is electro-osmotic or pressure driven. In another embodiment, the flow generating means is a pump. In another embodiment, the flow generating means is a reciprocating pump. In another embodiment, the flow generating means is a rotary pump. In another embodiment, the flow generating means is a mechanical pump. In another embodiment, the flow generating means is an electroosmotic pump. In another embodiment, the flow generating means is the native electroosmotic flow of the channel. In another embodiment, the flow generating means is any pump known to one of skill in the art. In another embodiment, the flow generating means or pump generates a continuous flow. In another embodiment, the flow generating means or pump generates a uniform outflow. In another embodiment, the flow generating means or pump generates a uniform pressure. In another embodiment, the flow generating means or pump can be adjusted in terms of its pumping capacity, its outflow generation, its pressure generation or any combination thereof.

In another embodiment, said at least one action is modulating (reducing, elevating or maintaining) the temperature in a pre-determined zone in said flow channel. In another embodiment, temperature modulation in a pre-determined zone in said flow channel is useful for enhancing analyte detection reaction. In another embodiment, said analyte is a nucleic acid molecule. As will be appreciated by a skilled artisan, various nucleic acid reactions which require temperature modulation steps (e.g., PCR or hybridization assays) may be used in the ITP apparatus and method described herein. None-limiting methods and devices for controlling temperature include external sources such as a peltier device or external electrodes, embedded heating elements (such as electrodes embedded in the channel), radiation, heating such as by increasing joule heating, and increasing or reducing heat dissipation from the flow channel.

In another embodiment, the action performed in response to an electric current/voltage change is operating a light source or imaging device. Operating, in one embodiment, is turning on the light source or imaging device. In another embodiment, operating is turning off the light source or imaging device. In some embodiments, the light is kept off to prevent photobleaching of a sample, and is turned on when the ITP interface (comprising the sample) approaches the detector. In another embodiment, said pre-determined period of time is of at least 1 second, of at least 5 seconds, of at least 10 seconds, of at least 15 seconds, of at least 20 seconds, of at least 25 seconds, of at least 30 seconds, of at least 40 seconds, of at least 50 seconds or of at least 60 seconds. In another embodiment, said pre-determined period of time is of at most 5 hours, at most 2 hours, at most 1 hour, or at most 0.5 hour. Each possibility represents a separate embodiment of the present invention.

It will be apparent to one skilled in the art that the effective pre-determined period of time varies according to the particular function/actions performed in response to an electric current/voltage change, such as, a pre-determined period of time of about 1 second is effective in functions such as modulating the temperature, addition of a compound or operating a light source/imaging device; however, longer periods of time (e.g., of at least 5 seconds) may be required for functions such as electric filed changes.

In another embodiment, said ITP method described herein is useful for diagnostic use. Non-limiting examples of diagnostic use include detection of pathogens such as in bodily fluids, water and food. None limiting examples of biomarkers include nucleic acids (e.g. 16S rRNA as a marker for bacteria) and proteins (e.g. HRPII as a marker for Malaria *plasmodium falciparum*), depending on the mature of the analyte.

In another embodiment, the method described herein is used for detecting a disease or disorder in a subject (e.g., a mammal and particularly human subject). It will be apparent to one skilled in the art than many disease-specific biomarkers (e.g., human miRNA) are known and can be used in the methods described herein. None limiting examples include prostate-specific membrane antigen (PSMA) for detection of prostate cancer and cTnI (cardiac trophonin I) for detection of cardiac damage. In another embodiment, the method described herein is used for detection of antibiotic resistance (e.g., by determining bacterial DNA). In another embodiment, the method described herein is used for detection of specific bacterial strains (e.g., by determining bacterial DNA).

In another embodiment, said ITP system, apparatus, kit and method described herein is useful for laboratory assays, including but not limited to ELISA and microarray chips.

In another embodiment, the leading electrolyte (LE) buffer is chosen such that its ions (cations or anions) have higher effective electrophoretic mobility than the ions of the trailing electrolyte (TE) buffer (also referred to as terminating electrolyte buffer (i.e., effective mobility describes the observable drift velocity of an ion under an electric field and takes into account the ionization state of the ion). In another embodiment, sample ions of intermediate effective mobility race ahead of TE ions but cannot overtake LE ions, and so they focus at the LE-TE interface (hereinafter called the "ITP interface"). In another embodiment, the LE and TE buffers are chosen such that the sample ions have a higher mobility than the TE, but cannot overspeed the LE. In another embodiment, the TE and LE buffers form regions of respectively low and high conductivity, which establish a steep electric field gradient at the ITP interface. In another embodiment, the LE buffer (or LE) has a high ionic strength. In another embodiment, the LE buffer (or LE) has a low ionic strength.

In another embodiment, ITP includes a microchannel connected to two reservoirs and is initially filled with LE solution. In another embodiment, a sample comprising an analyte to be detected is mixed in the trailing electrolyte (TE) reservoir. In another embodiment, a sample comprising an analyte to be detected is mixed in the leading electrolyte (LE) reservoir. In another embodiment, a sample comprising an analyte to be detected is injected between the LE and TE. In another embodiment, an electric field induces the electromigration of all ions in the channel.

The term "micro-channel" or "flow-channel" is used herein to refer to the flow path extending from at least one reservoirs to at least a second reservoirs. A schematic illustration of a typical flow channel connected to two reservoirs is illustrated herein in FIG. 1a, as a non-limiting embodiment.

In another embodiment, the term "detecting" includes labeling, separating, enriching, identifying, sorting, isolating, or any combination thereof. In another embodiment, detecting is quantitative, qualitative, or both.

In another embodiment, the present invention provides the ITP kit as described herein and specific instructions for performing the method as described herein. In another embodiment, the present invention provides a kit comprising an instruction manual describing the method and/or system disclosed herein. In another embodiment, the present invention provides a kit as described herein further comprising an electrophoresis apparatus. In another embodiment, the present invention provides a kit as described herein further comprising an electrophoresis apparatus that is communicatively coupled to a central processing unit (including but not limited to CPU, microprocessor, ASIC or FPGA) that may operate the electrophoresis apparatus based on a predetermined set of instructions.

In another embodiment, the present invention provides methods, systems and kits that reduce false positive or false negative results. In another embodiment, the present invention provides methods, systems and kits that reduce background noise. In another embodiment, the present invention provides methods, systems and kits that provide accurate quantitative measurements of analtyes of interest. In another embodiment, the present invention provides methods, systems and kits that provide an efficient separating technique for an analyte of interest.

In another embodiment, the present method requires minimal or no sample preparation. In another embodiment, the theory behind ITP is provided in Bahga S S, Kaigala G V, Bercovici M, Santiago J G. High-sensitivity detection using isotachophoresis with variable cross-section geometry. Electrophoresis. 2011 February; 32(5):563-72; Khurana T K, Santiago J G. Sample zone dynamics in peak mode isotachophoresis. Anal Chem. 2008 Aug. 15; 80(16): 6300-7; and Isotachophoresis: Theory, Instrumentation and Applications. F. M. Everaerts, J. L. Beckers, T. P. E. M. Verheggen, Elsevier, Sep. 22, 2011, which are hereby incorporated by reference in their entirety.

As used herein the term "disposable" refers to a design of an apparatus such that it is intended for use for a finite number of times and then discarded. Some disposable apparatuses are used only once and then discarded, such as for diagnostic uses. Other disposable components are used more than once and then discarded.

Figure 5:
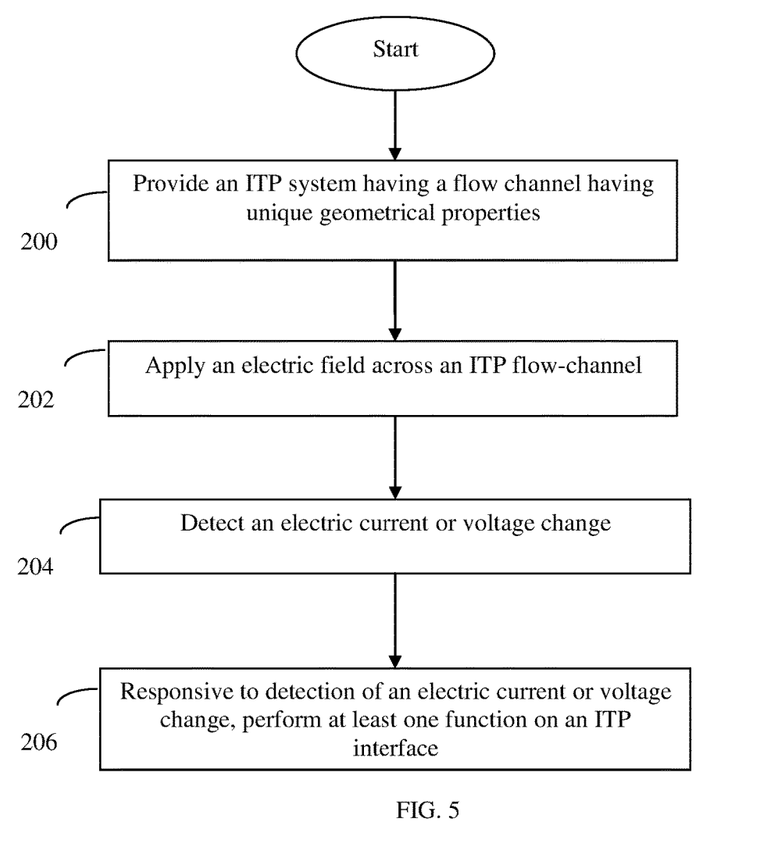
FIG. 5. An example flowchart demonstrating the steps for automating ITP.

Reference is now made to FIG. 5 which is a flowchart of a method for performing one or more automated function on an ITP interface. An ITP system as disclosed herein is provided (step 200). The ITP typically includes a microchannel having unique geometrical properties, connected to two reservoirs and is initially filled with LE solution. A sample comprising an analyte to be detected is mixed in the trailing electrolyte (TE) reservoir. Alternatively, a sample comprising an analyte to be detected is mixed in the leading electrolyte (LE) reservoir. Alternatively, a sample comprising an analyte to be detected is injected between the LE and TE. Subsequently, an electric field is applied, thereby inducing the electromigration of all ions in the channel (step 202). A measurement or control unit may be used for detection of an electric current or voltage change (step 204). Detection of an electric current or voltage change indicates the precise ITP location. Accordingly, one or more functions may be applied on the ITP interface, in response to measurement of current or voltage change (step 206).

Computer Program Product

In some embodiments, the ITP system or kit disclosed herein comprises a (disposable or permanent) ITP apparatus, a measurement apparatus configured to interact with said ITP apparatus, and a control unit configured to modulate an ITP interface of said ITP apparatus in response to a significant electric current or voltage change. In some embodiments, said measurement apparatus is configured to detect electric current and/or voltage changes (e.g., a rapid current drop). In some embodiments, said detection is performed using cross-correlation between a step function and the electric current or voltage measurement. The exact shape of the step function may be determined from preliminary experiments performed on the same geometry.

In some embodiments, the ITP apparatus, kit, system and method described herein comprise applying constant voltage and detecting current changes. In other embodiments, the ITP apparatus, kit, system and method described herein comprise applying constant current and detecting voltage changes.

In some embodiments, the correlation between the step function and the electric current/voltage signal is maximal at times where the shape of the current/voltage curve is most similar to step function. Local maxima in the cross-correlation signal may be detected, indicating passage through the constriction. A decision is then made and communicated (e.g. command to the power supply to turn off).

In another embodiment, at least two constrictions are used, wherein the first constriction is used as a learning step to construct the step function, which is then applied for detection of additional constrictions.

In another embodiment, the rate of the current/voltage changes (e.g., current decrease or voltage increase) in a straight channel (e.g. beginning of the channel) together with knowledge of the geometry is used to construct the step function.

In another embodiment, the change in current/voltage rate is detected by continuously calculating the local derivative of the current/voltage with respect to time. In another embodiment, the change in current/voltage rate is detected by continuously fitting a finite length of the electric current/voltage signal with a linear function.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

EXAMPLES

Automated ITP Detection Assays

ITP uses a discontinuous buffer system consisting of leading (LE) and terminating (TE) electrolytes (FIG. 1). The LE and TE are chosen to have respectively higher and lower electrophoretic mobility than the analytes of interest. Sample is injected between the TE and LE (or can be mixed with the TE in the reservoir). When an electric field is applied, ions whose electrophoretic mobility is bracketed between that of the LE and TE focus within an electric field gradient at the LE-TE interface. Design of the LE and TE chemistries enables selective focusing of species of interest, and exclusion of undesired species. Up to a million-fold increase in concentration in 2 minutes has been demonstrated. (Jung et al. Analytical Chemistry 2006)

ITP is typically used to focus a sample of interest and deliver a high concentration target to a pre-functionalized surface, thus enabling rapid reaction at the sensor site. A recent publication showed two orders of magnitude improvement in limit of detection (LoD) compared to standard continuous flow-based hybridization, in a 3 min ITP-based nucleic acid hybridization assay (Karsenty et al., 2014, Analytical chemistry, 86(6), 3028-3036. As shown in FIG. 2, the ITP interface in which the sample is focused, transverses by electromigration over the reactive surface. However, despite a 20,000-fold increase in sample concentration, signal is enhanced only 100-fold due to the short reaction time (2 sec) in which the sample overlaps with the surface. Allowing longer reaction times is key in exhausting the full potential of the technique.

In attempt to allow longer reaction without requiring user intervention for exhausting the full potential of the ITP technique, we developed a method which allows determining the exact location of the ITP interface in the channel from electric current measurements on, and stopping it precisely in the reaction site, allowing longer time for the reaction to take place.

Figure 3A:
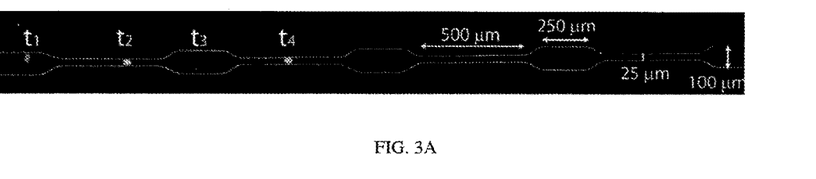
FIGS. 3a-c. Experimental results demonstrating the use of channel constrictions for accurate determination of ITP plug location. A constant voltage of 400 V was applied along the 5 cm channel (a) Overlay of 4 raw fluorescence images showing the location of the sample at different times during electromigration. (b) Corresponding electric current measurement vs. time. Electric field monotonically decreases as the low mobility TE displaces the high mobility LE. When the ITP interface enters a rapid and significant drop in current occurs. (c) We detect the transitions in real time by cross-correlation of the signal with a predefined step function. The method is robust to noise and peak values indicate the transition regions.
Figure 3B:
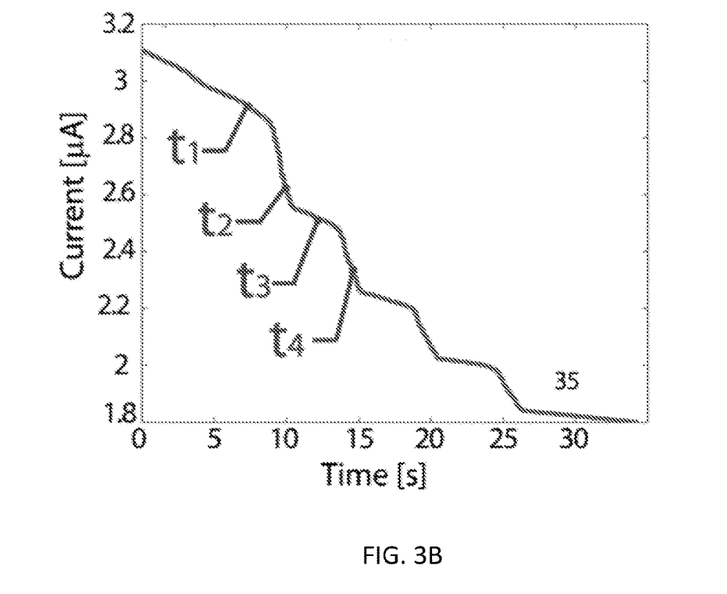
Figure 3C:
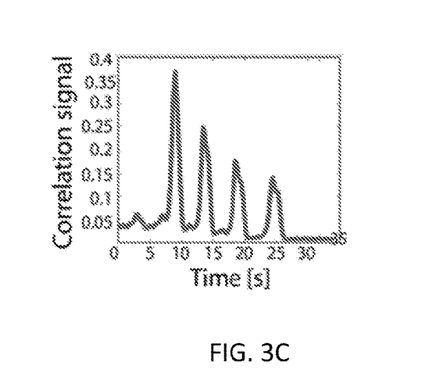

FIG. 3 presents experimental results demonstrating the principle of the assay; the microchannel design consists of a series of narrow constrictions. For constant applied voltage, current in ITP decreases monotonically due to increase in resistance. However, when the interface enters a constriction, this current drop is rapid and significant (FIG. 3b). These current drops can be easily and automatically detected (FIG. 3). Identification of the transitions between the wide and narrow sections of the channel may be used for cross correlation with a pre-defined step function. The peaks in the cross-correlation results correspond to the transition region.

Figure 4A:
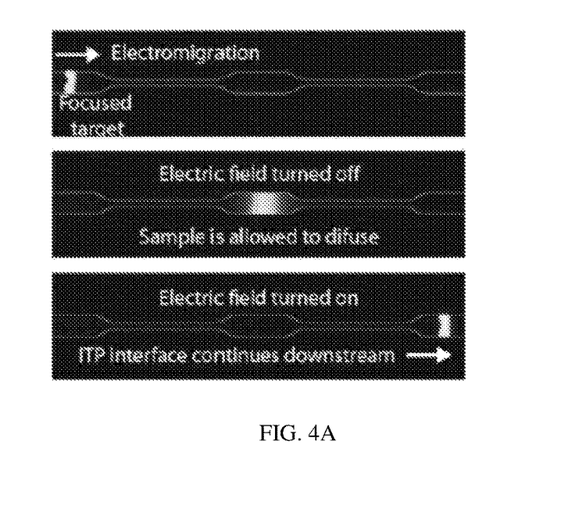
Figure 4B:
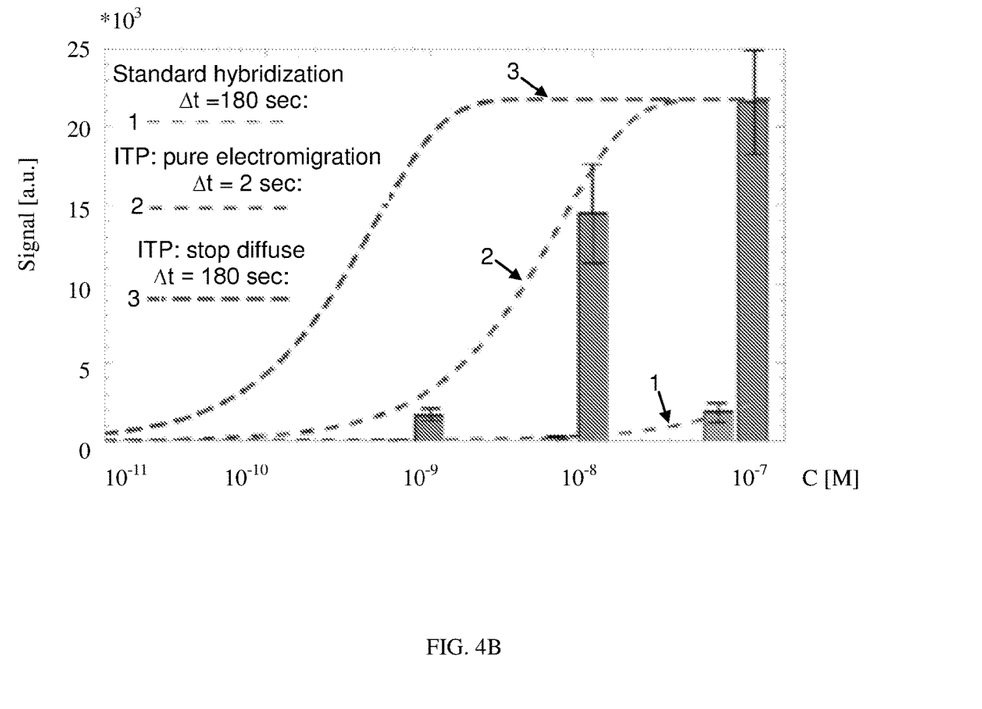

FIG. 4a presents experimental results in which the technique is used to deliver the concentrated ITP zone to a desired chamber. Upon arrival, the electric field is turned off and the sample is allowed to diffuse. After a fixed time allocated for reaction, the electric field is reestablished and the ITP interface continues electromigrating, removing any unreacted species from the surface. FIG. 4b presents the experimental results and model predictions for DNA hybridization under standard flow, pure ITP electromigration. Results show a 10-fold improvement over previous ITP-based assay, for a total of 1000-fold improvement compared to standard flow assay.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. An isotachophoresis (ITP) apparatus comprising:
   (a) a flow channel comprising at least one first cross-section area and at least one second cross-section area, wherein the ratio between said at least one second cross-section area and said at least one first cross-section area is of 1:2-1:50;
   (b) a first zone and a second zone, said first zone is configured to contain a solution of high effective mobility leading electrolyte (LE) ion, and said second zone is configured to contain a solution of low effective mobility trailing electrolyte (TE) ion; and
   (c) a control unit configured to modulate an ITP interface in response to a significant change to a rate of electric current decrease during constant voltage; optionally wherein said flow channel is configured to be operably connected to at least one anode and at least one cathode.

2. The apparatus of claim 1, wherein said ITP apparatus is permanent or disposable.

3. The apparatus of claim 1, wherein said modulation of the ITP interface is selected from the group consisting of:
   (a) substantially modulate the electric field for a pre-determined period of time;
   (b) apply a counter-flow for a pre-determined period of time;
   (c) modulate the temperature in a pre-determined zone in said flow channel; and
   (d) add at least one compound or composition to a pre-determined zone in said flow channel;
   or (e) a combination thereof;
   or wherein said modulation of the electric field is selected from the group consisting of: lowering the electric field, switching the electric field off, increasing the electric field or electric field path switching.

4. The apparatus of claim 1, wherein said significant change to a rate of electric current decrease or a rate of voltage increase is of at least 20% rate of change in said current decrease or said voltage increase.

5. The apparatus of claim 1, comprising any one of (i) an electric current or voltage sensor; and (ii) at least one regulator selected from the group consisting of:
   (i) an electric field regulator;
   (ii) a counter-flow regulator;
   (iii) a temperature regulator;
   or (iv) a combination thereof.

6. The apparatus of claim 1, wherein the control unit is configured to perform at least one function subsequent or concurrent to a significant change to a rate of electric current decrease or a rate of voltage increase.

7. The apparatus of claim 1, comprising a plurality of first cross-section areas and second cross-section areas.

8. The apparatus of claim 1, wherein said cross-section area ratio is of 1:2-1:25.

9. The apparatus of claim 1, wherein said second cross-section width is in the range of 5-100 μm.

10. The apparatus of claim 1, wherein said second cross-section has a length in the range of 20-500 μm.

11. A method for detecting an analyte of interest, comprising the steps of:
    (a) providing the ITP apparatus of claim 1;
    (b) providing a sample including at least one analyte of interest to the flow channel of said ITP apparatus; and
    (c) applying an electric field comprising constant voltage across said first zone and said second zone;
    wherein said control unit modulates an ITP interface in response to a significant change in a rate of electric current decrease or a rate of voltage-increase;
    thereby detecting the analyte of interest of interest.

12. The method of claim 11, wherein said modulating an ITP interface comprises at least one function selected from the group consisting of:
    (i) substantially modulating the electric field for a pre-determined period of time;
    (ii) applying a counter-flow for a pre-determined period of time;
    (iii) modulating the temperature in a pre-determined zone in said flow channel; and
    (iv) adding at least one compound or composition to a pre-determined zone in said flow channel;
    or (v) a combination thereof.

13. The method of claim 12, wherein said modulating the electric field is selected from the group consisting of: lowering the electric field, increasing the electric field or electric field path switching.

14. The method of claim 11, wherein said modulating an ITP interface increases reaction time for detecting said analyte of interest as compared to when said ITP interface is not modulated.

15. A kit comprising:
    (i) the ITP apparatus of claim 1;
    (ii) a solution of high effective mobility leading electrolyte (LE) ion; and
    (iii) a solution of low effective mobility trailing electrolyte (TE) ion; optionally
    (iv) comprising instruction for use of said kit.

16. A system comprising:
    (i) an ITP apparatus comprising:
       (a) a flow channel comprising at least one first cross-section area and at least one second cross-section area, wherein the ratio between said at least one second cross-section area and said at least one first cross-section area is of 1:2-1:50, and
       (b) a first zone and a second zone, said first zone is configured to contain a solution of high effective mobility leading electrolyte (LE) ion, and said second zone is configured to contain a solution of low effective mobility trailing electrolyte (TE) ion; and
    (ii) an electric current or voltage sensor; and
    (iii) a control unit configured to modulate an ITP interface of said ITP apparatus in response to a significant change to a rate of electric current decrease during constant voltage; optionally
       wherein said flow channel is configured to be operably connected to at least one anode and at least one cathode.

17. A computer program product comprising a non-transitory computer-readable storage medium having program code embodied thereon, the program code executable by at least one hardware processor to: (a) detect a significant change in a rate of electric current decrease during constant voltage in a flow channel comprising at least one first cross-section area and at least one second cross-section area, wherein the ratio between said at least one second cross-section area and said at least one first cross-section area is of 1:2-1:50; and (b) perform at least one function in response to the significant change of the rate of electric current decrease during constant voltage increase detected in step (a).

18. The computer program product of claim 17, wherein said performing at least one function is selected from the group consisting of:
    (i) substantially modulating the electric field for a pre-determined period of time;
    (ii) applying a counter-flow for a pre-determined period of time;
    (iii) modulating the temperature in a pre-determined zone in said flow channel; and
    (iv) adding at least one compound or composition to a pre-determined zone in said flow channel;
    (v) or a combination thereof.

* * * * *